United States Patent
Marcoz et al.

(10) Patent No.: US 12,016,998 B2
(45) Date of Patent: Jun. 25, 2024

(54) HANDHELD METERED DOSE INHALER

(71) Applicant: Biocorp Production S.A., Issoire (FR)

(72) Inventors: Alain Marcoz, Montmorin (FR); Alexandre Pereira, Perignat-les-Sarlieve (FR); Mathieu Pollard, Pont du Chateau (FR)

(73) Assignee: Biocorp Production S.A., Issoire (FR)

( * ) Notice: Subject to any disclaimer, the term of this patent is extended or adjusted under 35 U.S.C. 154(b) by 816 days.

(21) Appl. No.: 17/054,623

(22) PCT Filed: May 11, 2018

(86) PCT No.: PCT/IB2018/000685
§ 371 (c)(1),
(2) Date: Nov. 11, 2020

(87) PCT Pub. No.: WO2019/215471
PCT Pub. Date: Nov. 14, 2019

(65) Prior Publication Data
US 2021/0187214 A1 Jun. 24, 2021

(51) Int. Cl.
*A61M 15/00* (2006.01)

(52) U.S. Cl.
CPC ...... *A61M 15/0071* (2014.02); *A61M 15/009* (2013.01); *A61M 2205/3331* (2013.01); *A61M 2205/3365* (2013.01); *A61M 2205/50* (2013.01)

(58) Field of Classification Search
CPC .......... A61M 15/0065; A61M 15/0066; A61M 15/0068; A61M 15/007; A61M 15/0071; A61M 15/0073; A61M 15/0075; A61M 15/0076; A61M 15/0078; A61M 15/008
See application file for complete search history.

(56) References Cited

U.S. PATENT DOCUMENTS

| 5,809,997 A | * | 9/1998 | Wolf | A61M 15/0005 128/200.23 |
| 6,029,659 A | * | 2/2000 | O'Connor | A61M 15/009 128/200.23 |
| 6,360,739 B1 | * | 3/2002 | Rand | A61P 11/08 128/200.14 |

(Continued)

FOREIGN PATENT DOCUMENTS

| EP | 0387222 | 9/1990 |
| EP | 0617628 | 7/1993 |

(Continued)

*Primary Examiner* — Bradley H Philips
*Assistant Examiner* — Savannah L Gabriel
(74) *Attorney, Agent, or Firm* — Verrill Dana, LLP (57) ABSTRACT

The present invention relates to a metered dose inhaler (MDI) device comprising a mechanically activated visual cue representing a number of doses expelled from, or doses remaining in, a drug-containing cartridge or canister locatable within a body of said MDI, wherein the visual cue is visible through at least a portion of the body of said MDI, and a removable data processing system configured to verify the dose of drug administered and/or inhaled, wherein the MDI device further comprises a correlation system configured to correlate physically released doses from the drug containing cartridge or canister with the administration and/or inhalation data stored in the removable data processing system.

19 Claims, 5 Drawing Sheets

(56) References Cited

U.S. PATENT DOCUMENTS

| | | | | |
|---|---|---|---|---|
| 2002/0047021 A1* | 4/2002 | Blacker | ............... | G06M 1/041 |
| | | | | 222/23 |
| 2004/0044437 A1* | 3/2004 | DeVries | ............... | B65H 35/10 |
| | | | | 700/236 |
| 2008/0272834 A1* | 11/2008 | Uemura | ............... | G01D 5/145 |
| | | | | 327/544 |
| 2014/0216444 A1 | 8/2014 | Shtram | | |

FOREIGN PATENT DOCUMENTS

| | | |
|---|---|---|
| WO | WO2005079727 | 9/2005 |
| WO | WO2011144326 | 11/2011 |

\* cited by examiner

HANDHELD METERED DOSE INHALER

The present invention relates to hand-held metered dose inhalers, also known as MDIs, and more particularly to improving the observance of treatment regimes involved in the use of hand-held metered dose inhalers to dispense a metered quantity of drug. Such metered dose inhalers generally comprise a hollow body, into which a cartridge is inserted. The cartridge contains the drug to be dispensed or delivered, and the drug is generally formulated in such a way that when the cartridge dispensing mechanism is activated, the drug is released as an aerosol of drug particles or drug solution particles suspended in a gaseous vehicle, or the solution of drug is finely dispersed when released from a high pressure environment, such as the cartridge, to a lower pressure environment, such as the ambient environment of the user of the device.

One of the biggest problems with such devices is that, although they distribute metered, i.e. known predetermined quantities of active drug substance, it is very difficult to know whether the drug has been dispensed or delivered in accordance with the recommendations of the manufacturer or health care specialists that prescribe the treatment. This can lead to circumstances where the drug is not inhaled correctly by the user, e.g. through lack of correct coordination between activating release of the drug and inhaling, or simply wasted, for example in the case of accidental delivery of the drug, or even overdosed, for example, because the user thinks that previous attempts to inhale the drug have failed or were unsatisfactory. As such devices are often used for long periods of time, e.g. to correct or treat long term respiratory conditions such as asthma, the incorrect administration and usage of such hand-held metered dose inhalers can lead to other, more serious problems.

Several attempts to exert greater control over the delivery of the drug to be inhaled and provide some measure of reassurance, feedback or comfort to the user have been proposed over the years. Most of these attempts have focused at either integrating sensors and circuitry directly into the hollow body that receives the cartridge containing the drug to be dispensed, termed here for ease of understanding as the "integrated approach", or else relate to further devices that are added in some way onto the hollow body or cartridge. The latter solutions are termed "add-on" devices, because they can generally be added or removed from the hollow body, or cartridge, as and when needed, or say, for example, for cleaning or exchange of the device circuitry.

An example of the integrated approach is disclosed in European patent EP0617762. A hollow body is provided in which a drug dispensing cartridge is inserted, wherein the hollow body is equipped with an observance system, including visual and audible signals, and a display, to display messages to the user with regard to correct administration of the drug dispensed by the cartridge. The body is also provided with a channel or conduit, that allows for passage of air from the outside or ambient air, to pass through the hollow body and into a drug distribution mouthpiece outlet. Electronic sensor means are located within the channel in order to measure changes in air pressure flowing through the channel, and motion sensor means are provided for detecting if the canister is shaken prior to each actuation. The various signals obtained from the various sensor means are processed and relayed to the display to show an appropriate message to the user.

An example of the "add-on" device approach is disclosed in European patent EP0387222. This document describes a metered dose inhaler system that comprising a pressure filled canister and hollow body for containing said canister. The pressure canister is provided with a nozzle and is placed in a bracket with a nozzle. The bracket is shaped with a separable unit, which comprises a detector in connection with the air channel for the inhalation flow and an electronic unit. When the patient inhales from the mouthpiece, air flows are opened past the gap around the pressure canister and out through the mouthpiece. The patient has to, during the introductory phase of the inhalation, press the canister down, so that a dose is released through the nozzle. The air flow around the canister and the bracket give rise to a noise, which can be detected by a noise detector. When a dosage is released through the nozzle a sound arises, which can be distinguished from the noise and can be detected by the detector. Since these sounds are different from each other, a microphone can be used as detector. At inhalation through the inhaler according to FIG. 7, a pressure drop is created between the ambient pressure and the pressure at the mouthpiece opening, i.e. a sub-pressure arises inside the bracket when the patient inhales, which sub-pressure can be detected by a pressure transmitter. At the release of a dose, a strong pressure change with short duration arises, which is also detectable by a pressure transmitter. In the embodiment according to FIG. 7, a pressure transmitter can also be used for detection of both the inhalation and the release of a dose, i.e. the information necessary for controlling that the patient uses the dose aerosol in the prescribed way.

Unfortunately, the known solutions from the prior art are particularly complex to design and manufacture and fail to address a number of problems associated therewith. In particular, the known solutions from the prior art, such as the ones exposed above, fail to deal with the issue of being able to physically measure the number of pressurised drug releases from the cartridge or canister containing the aerosol drug, and accurately correlate that number with the data registered by the provided inhalation processing system. This problem becomes especially acute when, for example, the power supply for the data processing system is absent or depleted, as can happen when the processing and signalling system built into such devices is powered by a rechargeable battery, for example. In such moments, the metered dose inhaler will either be incapable of being operated by the user to administer required drug doses, essentially rendering the MDI useless, or else it will simply not register any drug released from the canister or cartridge with the processing system when the user activates it to administer a corresponding required dose of drug.

Prior to the emergence of MDI devices as described above having on-board data processing systems, releases of drug doses, i.e. the number of presses on the mechanical release system of the cartridge or drug container, were displayed visually via an opening provided in the body surrounding the canister or cartridge or drug container. These visual displays were often provided by a wheel or visual counter, that was moved mechanically and physically indexed to one or other of the moving parts involved in the release of a drug dose. However, these physically and mechanically connected visual displays were unable to provide any indication of actual drug inhaled, or any real notion of independent observance of a drug treatment regime.

One object of the handheld metered dose inhaler device of the present invention is therefore to provide a MDI device comprising a mechanically activated visual cue representing the number of doses expelled from or doses remaining in a drug-containing cartridge or canister, and a removable data processing system configured to verify the dose of drug administered and/or inhaled, wherein the MDI device further comprises correlation means configured to correlate physically released doses from the drug containing cartridge or canister with the administration and/or inhalation data stored in the removable data processing system.

Such a system overcomes the limitations and problems described above with regard to known prior art solutions. In addition, such a combination provides further advantages as follows:

- it becomes possible with the handheld device according to the invention to reduce the overall bulkiness of the cartridge holder body, whilst still being able to continue to use the handheld MDI device, making it suitable for use, for example, by children;
- it becomes possible for the data processing system of the MDI device, if such a system includes an autonomous power supply, to be recharged separately from the MDI device, or even exchanged should the data processing system become defective for whatever reason;
- the data processing system can be configured to synchronize the data stored therein with a remote observance system without having to be physically connected to the MDI device, leaving the MDI device available for continued use by the patient.

These and other advantages will become apparent as the further objects of the invention are exposed hereafter.

According to another object of the invention, the correlation system comprises mechanical activation means in contact with a drug containing cartridge of the MDI device, and wherein said mechanical activation means engage with translational movement conversion means configured to convert a translational movement of the mechanical activation means into a rotational movement. In typical metered dose inhalers, when the drug cartridge is activated to expel a dose of drug, a downwards press is made by the user on the top of the cartridge seated within the inhaler body, the downward press of the cartridge thereby depressing a spring-loaded valve, which opens into the drug cartridge, and said drug, being contained under pressure within the cartridge is released to the environment via the inhaler body and channeled via the user's mouth into the user's respiratory system. This mechanical activation means are in contact with at least a part of the drug cartridge so that when the cartridge is moved downwards by the user's press, it also moves in a generally downwards direction. The mechanical activation means of the correlation system thereby come into contact with or engage suitably disposed translational movement conversion means. The translational movement conversion means are configured to convert the generally downwards, translational movement of the pressed drug cartridge transmitted via the mechanical activation means into a rotational movement.

According to one object of the invention, the mechanical activation means in contact with a drug containing cartridge of the MDI device comprise a spring-loaded tongue having a first extremity and a second extremity, said first extremity engaging with a collar of said drug containing cartridge, and said second extremity engaging with the translational movement conversion means configured to convert a translational movement of the mechanical activation means into a rotational movement.

An example of a suitable mechanical activation means embodied by the spring loaded tongue above is, for example, and concretely, a spring-loaded caliper, or stirrup, which is seated in contact with a shoulder of the drug cartridge or canister, and held in contact therewith by a spring. The spring is seated at one end against a substantially horizontally projecting wall which extends from a substantially vertical body wall of the inhaler and maintains the tongue, or stirrup, against the body of the canister or cartridge in a relaxed or extended configuration. The tongue, or stirrup, sits over the circumference of the spring at another end thereof, and comprises at least one projecting tine that projects from a tongue or stirrup body into an inner axial bore defined by the helix of the spring. The stirrup further comprises a stirrup leg extending downwardly from the stirrup body, and outside of the circumference of the spring. At a lower extremity of the stirrup leg, a hooked, curved, or pointed tip is provided. Preferably, this stirrup leg, and optionally the stirrup leg tip, are made of a pre-constrained material, that enables the tongue, or stirrup leg and tip, to deform or flex in a desired and predetermined manner, for example, showing a degree of hysteresis. The second extremity of the tongue, herein exemplified as the stirrup leg tip, comes into contact, and engages with, a corresponding translational movement conversion means to convert said translational movement into a rotational movement when the canister is depressed or activated by the user.

According to yet another object of the invention, the translational movement conversion means comprises an axle shaft having a peripheral surface, said peripheral surface being engaged by the second extremity of the spring loaded tongue at each activation of the drug-containing cartridge or canister, and imparting a rotational movement to said axle shaft. In the embodiment described above, the tongue is exemplified by the stirrup leg and the stirrup leg tip corresponds to the second extremity of the tongue, which comes into contact with the peripheral surface of the axle shaft.

The rotating axle shaft is advantageously mounted substantially beneath the second extremity of the tongue, or as herein exemplified, the stirrup leg tip, and orthogonally in relation the direction of movement of the tongue or stirrup leg tip. Downward movement as described above, when the cartridge or canister is depressed, causes the spring to be compressed into a constrained configuration, and the tongue, or stirrup leg, moves down at the same time, bringing the second extremity of the tongue, i.e. the stirrup leg tip, into contact with the axle shaft. When pressure on the canister is released, in other words, usually when the user releases hand or finger pressure on the top of the canister, the tongue, or stirrup leg and tip, is/are moved back to their initial relaxed position away from the axle shaft under the effect of the seating spring recoil as the spring moves back to the unconstrained position.

The axle shaft further comprises an outer surface which comes into contact with the second extremity of the tongue, or as exemplified, the stirrup leg tip. Advantageously, this axle outer surface is sculpted or shaped to receive the second extremity of the tongue, or stirrup leg tip, as it moves downwards into contact with the axle surface, and upon further downward travel of the tongue, or stirrup leg tip, cause the axle to rotate about the axles axis of rotation. Each downward movement, in other words, each depression of the canister, coincides with a single travel distance of the tongue, or stirrup leg and tip, and a corresponding contact and transmitted angle of rotation of the axle shaft.

According to yet another object of the invention, the peripheral surface of said axle shaft is provided with a plurality of peripheral teeth projecting from said peripheral surface, a different tooth of the plurality of peripheral teeth engaging with said second extremity of said tongue at each activation of the drug-containing cartridge or canister. In order to ensure regular and a sufficiently consistent angular rotation of the axle shaft, the axle shaft outer surface is provided with a series of teeth. The gorges of the teeth thus provide at least one bearing surface with which the second extremity of the tongue, or as exemplified, the stirrup leg tip, can come into contact and push the axle shaft around its axis of rotation. The hooked, curved or pointed second extremity of the tongue, or stirrup leg tip, is shaped so that while it engages with the surface of the axle shaft during the downward movement, it disengages from said axle surface on the return, or upward movement, for example after the tip has passed a tangential point of contact on said axle shaft surface. This can be obtained as indicated above by making the stirrup leg, and/or tip, out of a pre-constrained, resilient and/or semi-flexible material with a smooth axle-surface facing surface such that, when the tip begins its return upward journey, the tip flexes away from the axle surface and slides over the latter without engaging said axle surface to rotate the axle in a reverse direction. In this way, a translational movement is not only converted into a rotational movement, but additionally, said rotational movement is a unidirectional rotation. Naturally, whilst the present invention has been described with the above configuration in mind, other mechanisms for converting translational movement into a suitable rotational movement can also be used and are considered to lie within the scope of the present invention.

According to another object of the invention, the correlation system further comprises at least a first rotational position sensor. The first rotational position sensor is configured to measure the angle of rotation through which the axle shaft has turned after a downward translational contact event from the stirrup leg tip. Advantageously, the first rotational position sensor is coupled in an appropriate way to the axle shaft, and even more advantageously, coupled in an indexed manner, so that any rotational movement of the axle shaft correlates directly to a precise measurable angle of rotation within the sensor.

According to yet another object of the invention, the correlation system further comprises at least a second rotational position sensor.

According to a still yet further object of the invention, the at least first rotational position sensor and/or the at least second rotational position sensor are configured to convert an angle of rotation into an electrical signal.

Whilst various ways of implementing the above are possible, the applicants have found that using a potentiometer as the first and/or second rotational position sensor is particularly advantageous as potentiometers convert rotational movements into electric potentials, the values of which can be stored in a suitable memory module provided, for example, on suitable small circuit board. In such a case, the potentiometer is advantageously a single-revolution rotary potentiometer, i.e. configured to only measure an angle of rotation up to a maximum of a single complete revolution of the potentiometer, or alternatively, a multi-revolution rotary potentiometer, i.e. configured to measure angles of rotation over several complete revolutions of the potentiometer. For example, the CS14 range of rotary potentiometers commercialized by the Spanish corporation ACP have been found to be suitable for use in the device of the invention. Rotary potentiometers as envisaged for use in the present application are provided with a generally central opening, into which is inserted the axle shaft of the translational movement conversion means. The outer, axle shaft surface engages with a switch in the potentiometer causing said switch to move in a substantially circular arc, thereby causing an electric potential to be generated. The electric potential is communicated to a circuit board comprising either a processing unit, and/or a memory module for storing the value of that electric potential. Each electric potential measured or registered from the potentiometer, which in turn is generated by corresponding rotational movement of the axle shaft, respectively corresponds to an angle of rotation. The calculated angles of rotation resulting from the measured electric potentials can thus be used to determine how many doses of drug have been expelled from the canister, as each downward press is converted to a rotational movement, and thus an electrical signal.

Of particular advantage is a configuration in which a first rotary potentiometer is a single-revolution potentiometer, and a second rotary potentiometer is multi-revolution potentiometer. By providing a suitable and appropriate connection between the two differently configured potentiometers, it is possible to calculate a whole range of angles and precision, including the number of revolutions that the axle shaft has been rotated.

Accordingly, and as will be understood from the above description, the translational movement conversion means, for example as indicated in the preceding paragraph, the axle shaft, is connected to the at least first rotational position sensor.

According to yet a still further object, the at least first rotational position sensor is configured to effect no more than one revolution of said sensor before a reset. In such a case, a single-revolution rotary potentiometer is preferred.

According to yet a still further object, the at least second rotational position sensor is configured to effect at least a plurality of revolutions of said sensor before a reset. In such a case, a multi-revolution rotary potentiometer is preferred.

According to yet another embodiment of the invention, the at least first rotational position sensor is mechanically connected to the at least second rotational position sensor, and a rotational movement imparted to said at least first rotational position sensor is communicated to said at least second rotational position sensor. The second rotational position sensor, when present, is thus preferably not mounted on the axle shaft, but is nonetheless mechanically connected to the first rotational position sensor. The mechanical connection between the first rotational position sensor and the second rotational position sensor provides for an indexation between said two position sensors, and preferably and advantageously the second rotational position sensor is indexed to the angle of rotation of the at least first rotational position sensor.

According to a still further object, the at least first rotational position sensor is connected to said at least second rotational position sensor via a visual display wheel mounted in coaxial rotational movement on said at least second rotational position sensor. In this case, the visual display wheel is for example mounted on an axle shaft that is inserted into a central opening of the second rotational position sensor. Thus any angles of movement that are translated to said second rotational position sensor via the mechanical connection between it and said first rotational position sensor are further communicated to said wheel, which rotates in tandem with the second rotational position sensor due to insertion of the wheel's axle shaft into the central opening of the second rotational position sensor.

According to still a yet further object, the visual display wheel comprises a wheel outer surface, a portion of which is visible through the body of the MDI, and wherein said wheel outer surface comprises markings representative of a number of doses remaining, or expelled, from the drug containing cartridge. In this manner, the user can instantly see how many doses of drug have been expelled, or remain, depending on how the device has been configured to count dose release.

According to yet another object, the correlation system further comprises a signal processing unit for processing signals received from the at least first rotational position sensor and/or the at least second rotational position sensor. The signal processing unit is configured for either receiving and storing values of electrical potential and/or angles of rotation generated by the at least first and/or second potentiometers, and/or for calculating angles of rotation from said electrical potentials. These values and/or angles are advantageously stored in a memory module provided within the body of the inhaler, for example located underneath the axle shafts.

According to yet a still further embodiment, the axle shaft of the translation conversion means further comprises a terminal toothed cog, located at an extremity of said shaft distant from said plurality of peripheral teeth. As mentioned above, and in accordance with another object of the invention, the axle shaft traverses and engages with an opening provided in said at least first rotational position sensor.

Furthermore, and according to a still yet further object, the toothed cog extends beyond the opening provided in said at least first rotational position sensor, such that said toothed cog is located outside of said at least first rotational position sensor. If one were to view the first positional sensor from the side, one would observe the axle shaft traversing the central opening of the sensor, and on the one side at an extremity of the axle shaft, the toothed cog standing proud, and ready to be engaged, and on the other side, the plurality of peripheral teeth disposed around a peripheral surface of the axle shaft.

As mentioned above, the first and second rotational position sensors are connected to each other via a mechanical connection. To that extent, a further object of the invention provides that the at least first rotational position sensor and the at least second rotational position sensor are connected to each other via a reducing gear having a first gear cog, a second gear cog, and an axle shaft connecting said first and second gear cogs, and on which said gear cogs are mounted at respective ends of said gear cog axle shaft, the first gear cog being located in mating and rotational contact with the toothed cog of the translational movement conversion means axle shaft, the second gear cog being located in mating and rotational contact with the visual display wheel. In this way, rotational movement of the translational movement conversion means axle shaft is transmitted via the toothed cog thereof to the first gear cog of the reducing gear. As the first gear cog is connected to the gear cog shaft, said shaft rotates as the toothed cog rotates, and causes the second gear cog to rotate accordingly. The second gear cog, being in rotating contact with the visual display wheel, causes said display wheel to rotate, thereby changing the reading of the dose expelled or remaining at the corresponding window. Additionally, as the visual display wheel is connected via a display wheel axle to the second rotational position sensor, said second sensor also generates a corresponding electrical potential, which can be measured or processed by the signal processing unit and optionally stored in memory.

According to yet a still further object, the removable data processing system comprises at least one air pressure sensor. This air pressure sensor can be advantageously configured to detect a change in air pressure when drug is inhaled by the user and/or expelled from the MDI. To this end, and according to yet another object, the at least one air pressure sensor is generally located within the body of the MDI device in proximity to an air flow passage.

According to yet another object of the invention, the at least one air flow passage is distinct from a passage for inhalation of expelled drug from the drug-containing cartridge. This is most advantageous compared to some known MDI devices which are equipped with air sensors, as including an air sensor in the inhalation passage itself can deleteriously affect drug flow in said inhalation passage, and furthermore lead to confusing or inaccurate readings of user inhalation, thereby reducing the accuracy of any observance data that might be collected from the presence of such an air pressure sensor.

According to yet a still further object of the invention, the removable data processing system is housed within a housing that is removable from and snap-fit insertable into, the body of the MDI device. In this way, it becomes possible to use the MDI even when the data processing system is not present, which is of significant advantage to most users of such devices, as they can rarely afford not to be able to use their inhalers, or nor can they generally afford to be obliged to switch from a purely manual inhaler device to an electronic MDI for the period of time that the electronic inhaler might be out of action for whatever reason.

According to a still yet further object of the invention, the housing for said removable data processing system further comprises an electrical contact for establishing an electrical contact with the correlation system when said housing is inserted in the body of the MDI device. The electrical contact of the removable data processing system is provided to enable an electrical contact between said removable data processing system and the collected data of the correlation system when the removable data processing system is re-introduced back into the MDI body, so that the data processing system can recover any such data from the correlation system and correct, register or calculate any changes in, say, the number of doses remaining and/or expelled, and the like.

To that end, and according to yet another object, the housing for said removable data processing system further comprises a power supply for supplying power to said data processing system and said correlation system. Such a power supply can be a portable power supply, for example, one or more suitable batteries, or a rechargeable battery system if such is deemed suitable and/or appropriate. Generally, a sufficient power supply can be provided through the use of a single battery, such as a lithium ion battery, of the type commonly found powering other low powered electrical devices such as watches, domestic smoke alarms, toys and the like.

BRIEF DESCRIPTION OF THE FIGURES

The invention will be detailed hereinafter by reference to the following figures, given as an illustration of the various objects and embodiments of the invention, and in which.

DETAILED DESCRIPTION AND EXAMPLE

Figure 1:
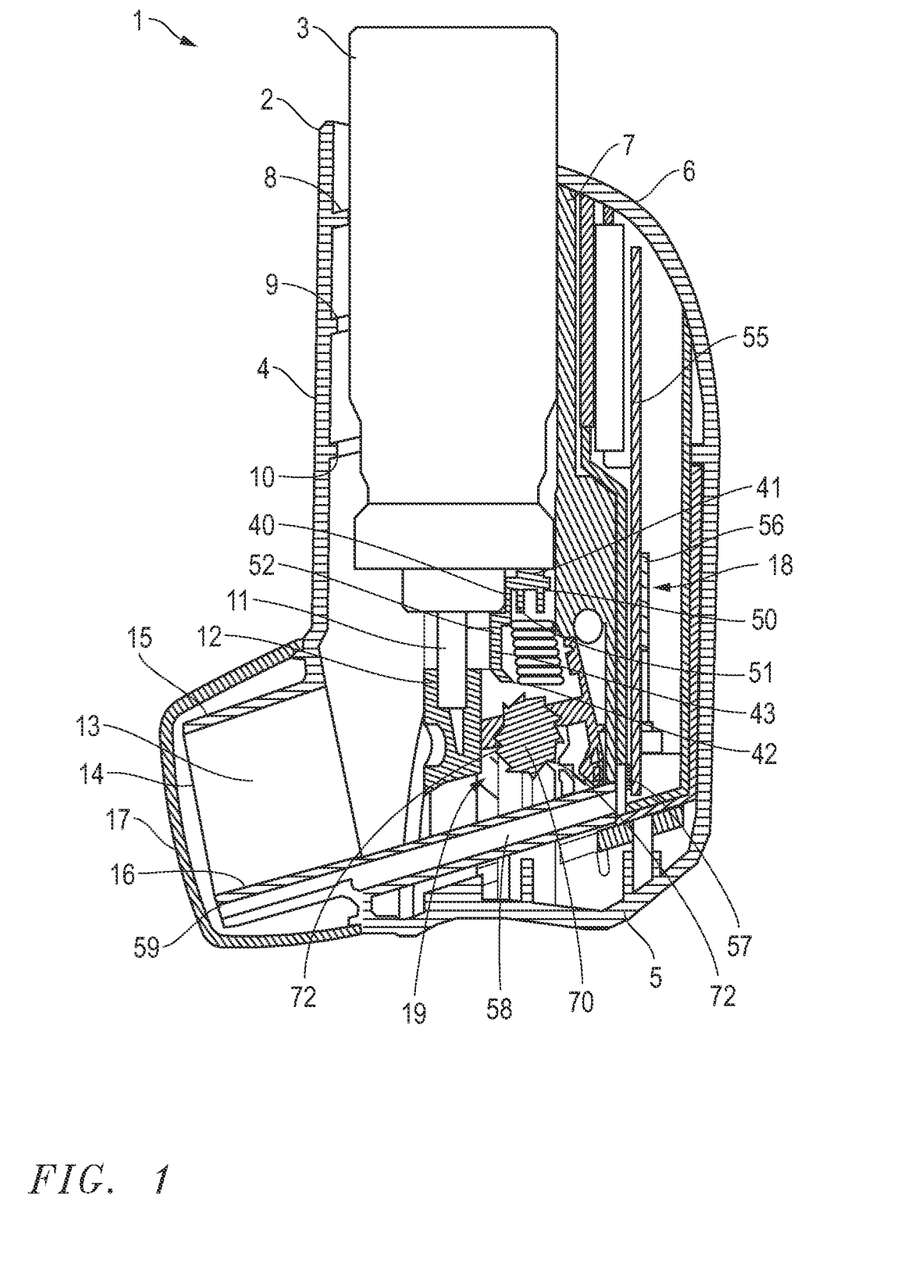
FIG. 1 is a schematic cross-sectional representation of a metered dose inhaler (MDI) device according to the present invention.

Turning now to FIG. 1, a metered dose inhaler (MDI) device is represented in an upright position in schematic cross-section and indicated the general reference numeral (1). The MDI (1) comprises an inhaler body (2), and a drug containing canister (3) located within said body (2), which when activated is generally configured to release the drug as an aerosol or a powder suspension in propellant gas. The upright position for such an inhaler is the usual presentation position for use of the MDI. The drug canister (3) is seated within the body (2) by the peripheral walls (4, 5, 6, 7) of the body and a series of projecting spars (8, 9, 10) extending out from at least one of the peripheral walls (4). The drug canister is held in the body (2) in a generally inverted position, with a release valve nozzle (11) located at a lower extremity of the canister from which the drug is expelled when the canister is activated. The release valve nozzle (11) is seated in a drug release channel (12) through which drug released from the canister (3) when activated is channeled into a drug flow passage (13) leading to an exit orifice (14) of the MDI body (2), the drug flow passage (13) and exit orifice (14) being defined by two substantially parallel extending projections (15, 16) of body wall material that is shaped and contoured to provide to be inserted into and fit inside a user's mouth, and be held therein during inhalation of the drug by closure of the mouth around the exit orifice. The MDI further comprises a removable data processing system, indicated generally by the reference numeral (18), configured to verify the dose of drug administered and/or inhaled, as will be described in more detail hereinafter, and a correlation system, indicated generally by the reference numeral (19), configured to correlate physically released doses from the drug containing cartridge or canister with the administration and/or inhalation data stored in the removable data processing system. Further details hereof will be given below.

Figure 2:
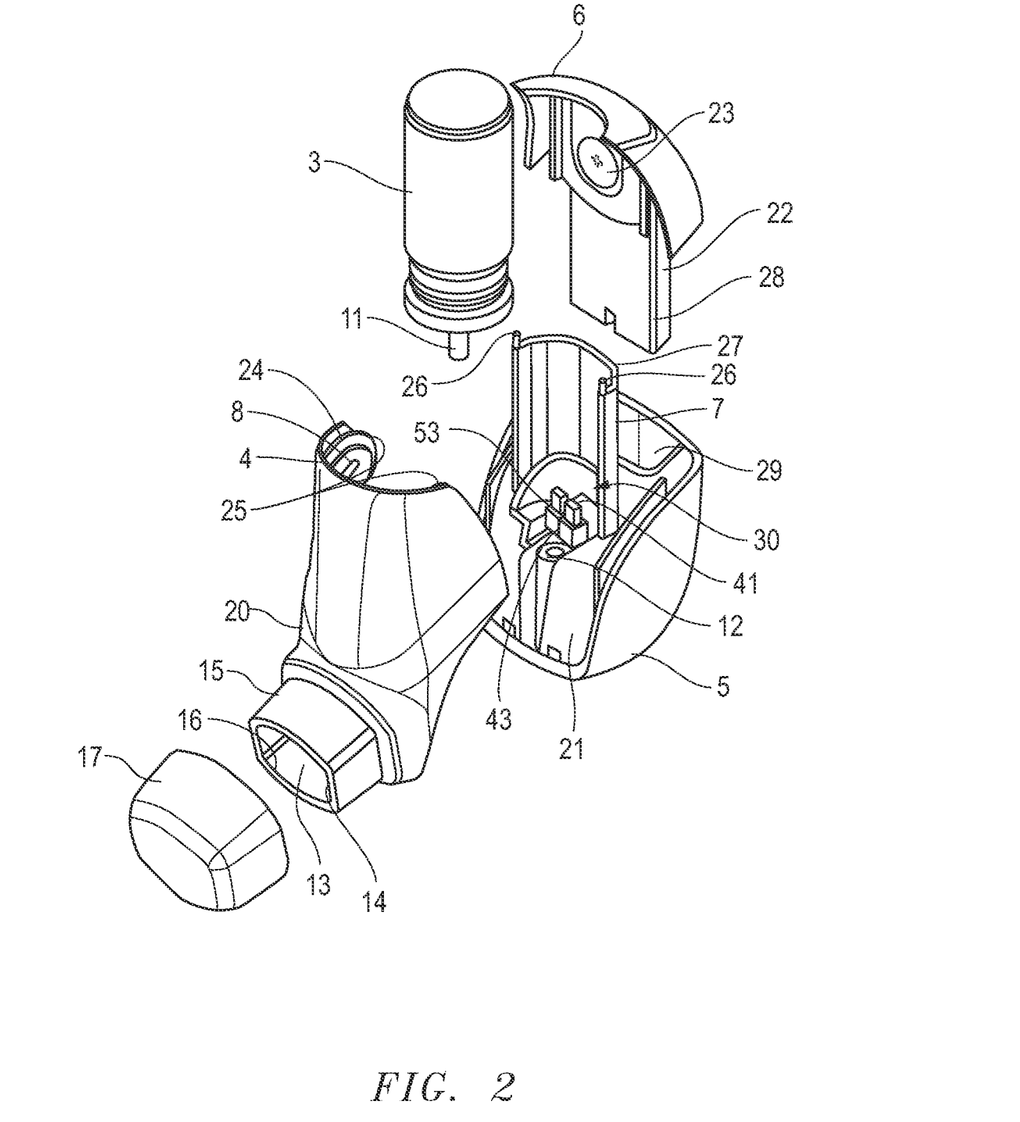
FIG. 2 is a schematic exploded perspective view of a metered dose inhaler (MDI) device according to the present invention.

FIG. 2 is an exploded perspective view representation of the MDI device (1) of FIG. 1, illustrating a set of sub-components of the device (1) that can appropriately be assembled to form the MDI device of the invention, and showing the inhaler device body (2) split into various complementary assembly parts, for example, prepared as injection-moulded parts, or machined assemblies that can be snap-fitted together to form the complete MDI body into which the canister (3) is inserted. The assembly of FIG. 2 illustrates in particular:

a front facing part (20) comprising body wall (4), and projecting spar (8), the drug flow passage (13) and exit orifice (14) defined by substantially parallel extending projections (15, 16) of the body wall;

a protective cap (17) configured to fit over the exit orifice (14)

a drug canister (3) with valve nozzle (11);

a correlation system housing (21), comprising body wall (7), and configured to house the correlation system (19), but also comprising the drug release channel (12) for seating the valve nozzle (11) of the canister (3); and a data processing system housing (22), comprising body wall (6), and configured to house the data processing system (18) (not shown), and further comprising a power supply housing (23), for receiving and covering a removable power supply, for example a typical lithium or optionally rechargeable battery.

As will be understood from FIG. 2, the front facing part is provided with an inner edge projection (24), said inner edge projection (24) comprising locating holes (25), which are located over, and onto, corresponding projections (26) provided in an upper edge surface (27) of body wall (7). Additionally, a lower part (28) of the data processing system housing (22) is inserted into a correspondingly shaped housing (29) provided within the correlation system housing (21), and body wall (6) meets with, and substantially covers the upper edge surface (27) of body wall (7) to complete the formation of the MDI device body into which the canister is inserted and located in drug release channel (12).

Additionally, FIG. 2 illustrates part of the correlation system (19) housed by correlation system housing (21), and in particular, mechanical activation means, indicated generally by the reference numeral (30), as will be described in more detail hereinafter.

Figure 3:
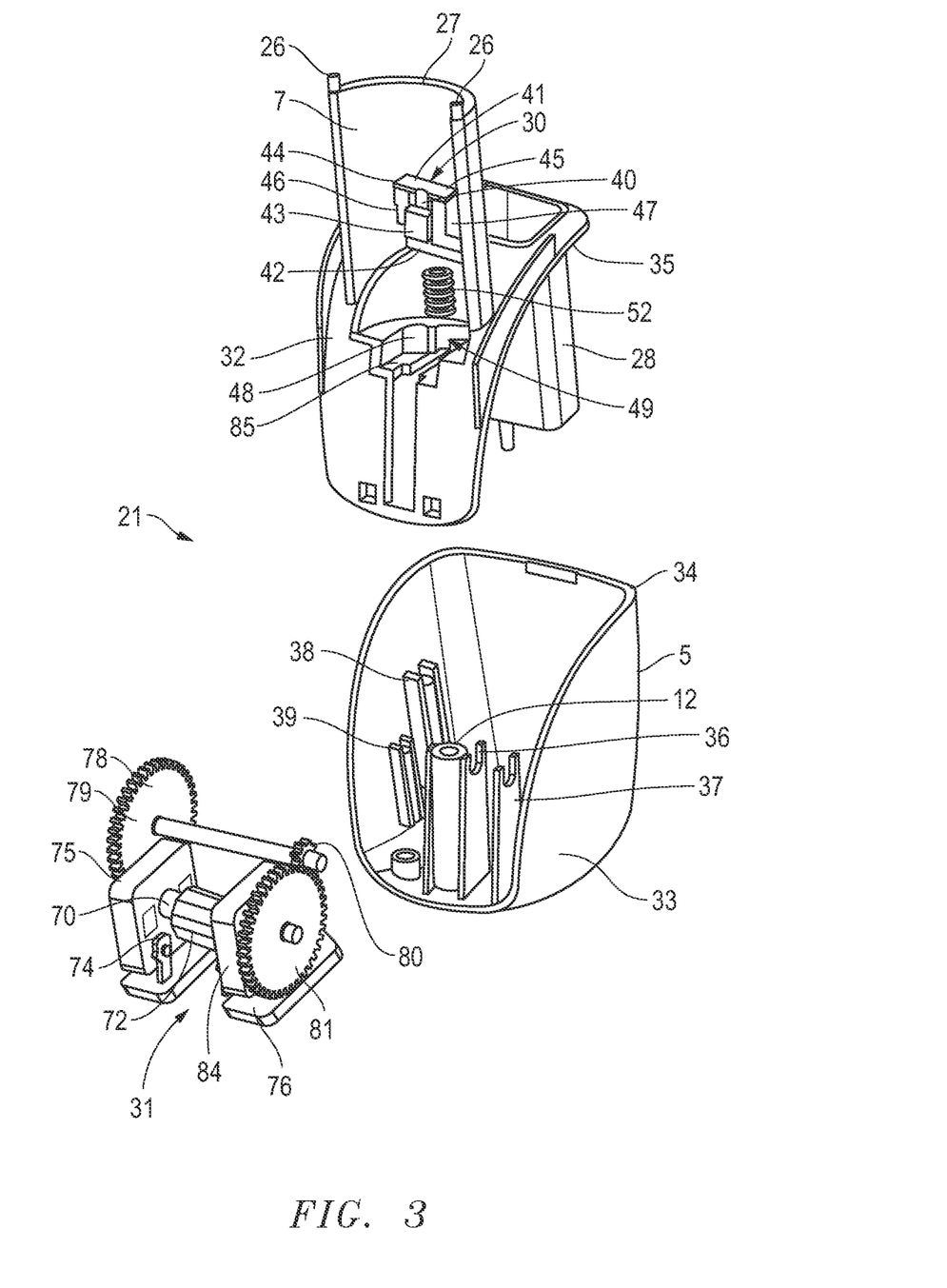
FIG. 3 is a schematic exploded perspective view of some of the detailed embodiments of a metered dose inhaler (MDI) device according to the present invention.

FIG. 3 illustrates a schematic exploded perspective view of the correlation system housing (21) and various subassemblies constituting, or included within, said housing (21). The exploded view shows various parts of the correlation system (19), in particular the translational movement conversion means, indicated generally by the reference numeral (31), and two correlation system housing complementarily shaped upper (32) and lower (33) housing components, for example made of moulded or machined material that fit together to form the correlation system housing (21). The upper housing component (32) is shaped to be insertable into, and interlockable with, the lower housing component (33), the lower housing component (33) having a peripheral upper surface edge (34) of body wall (5) which supports a lower surface (35) of the upper housing component (32). The lower housing component (33) also comprises appropriate seating and locating projections (36, 37) for receiving, seating and locating parts of the translational movement conversion means (31) within the lower housing component (33), and further seating grooves (38, 39) provided on an inner surface of body wall (5) to assist in receiving and seating the upper housing component (32), which is provided with corresponding and complementary seating projections (not shown).

As is further apparent from FIG. 3, the mechanical activation means (30) are illustrated. These comprise a tongue (40), or stirrup, having a first, upper extremity (41) and a second lower extremity (42), with a stirrup leg (43), extending from the first, upper, extremity (41), towards the second, lower, extremity (42), or stirrup tip. The first, upper, extremity (41) of the stirrup (40) comprises a substantially horizontal bar of material, for example, a suitable plastic material, having a first end (44) and a second end (45), with each end comprising a respective downward facing projection (46, 47). The downward facing projections (46, 47) are configured and dimensioned to be inserted, and slidingly fit, into correspondingly dimensioned receiving bores (48, 49) provided on the upper housing component (32). The stirrup (40) further comprises at least one downward facing projection (50, 51) extending from beneath the upper extremity (41) and located substantially in a central part thereof, which is inserted into the inner bore volume defined by a helical spring (52) at an upper extremity of said spring. The helical spring (52) is seated at its lower extremity on a wall portion that projects substantially horizontally outwards from body wall (7). The stirrup further comprises a shoulder located on the leg (43) which is located, when the device is assembled, in abutting relationship with a shoulder of the canister (3). This configuration enables the stirrup to be biased downwards when the canister is depressed, as the shoulder of the canister (3) presses down on the shoulder of the leg (43) of the stirrup (40), with the bar of the upper extremity (41) pressing against the spring (52) to compress it into a constrained position or configuration. For as long as downward pressure is maintained on the canister, the canister shoulder bears down on the stirrup shoulder, maintaining the stirrup leg (43) and tip (42) in a downwards position. When pressure on the canister is released, for example, by a user moving its fingers away from the top of the canister, the spring (52) pushes back against the bar of the upper extremity (41) of the stirrup (40), moving the stirrup leg (43) and tip (42) upwards back towards an unconstrained, or relaxed, position or configuration.

Figure 4:
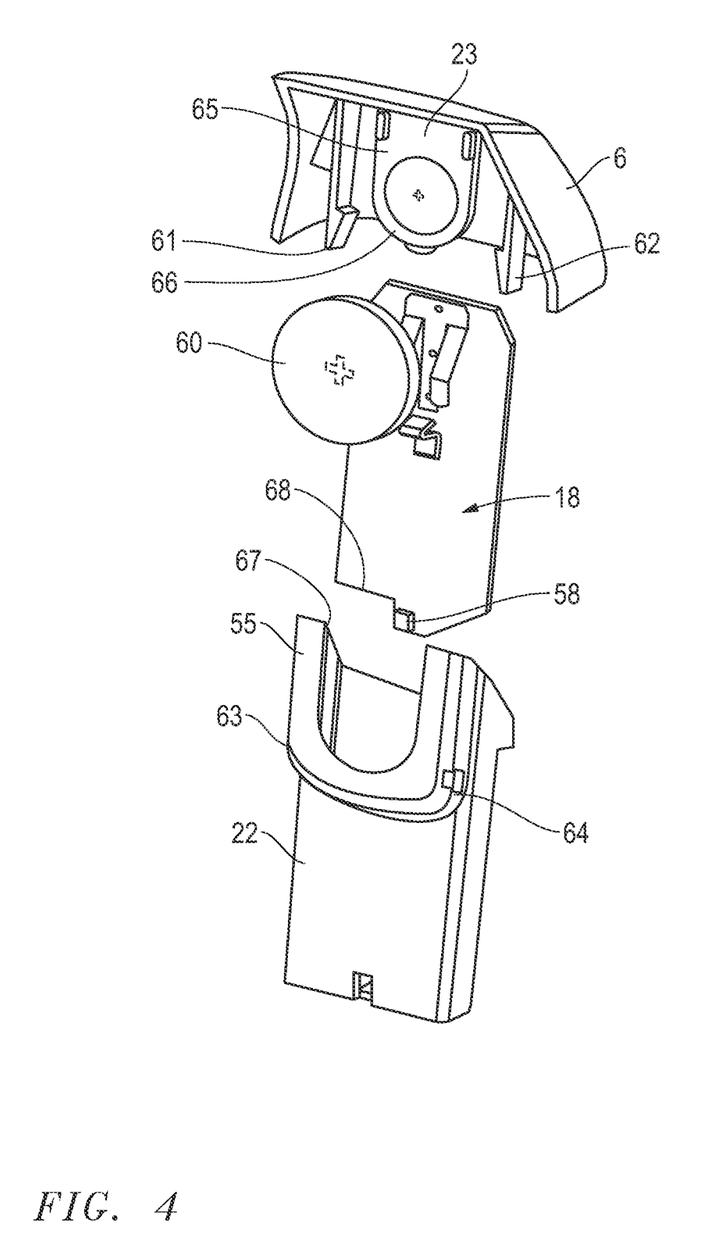
FIG. 4 is a schematic exploded perspective view of other detailed embodiments of a metered dose inhaler (MDI) device according to the present invention.

FIG. 4 shows a schematic exploded perspective view of the data processing system housing (22). The data processing system (18) is housed within this housing (22) and comprises, for example, a printed circuit board (55), including one or more data processing unit (56), and one or more signal handling units, used to process data, signals and events received and/or observed, and/or calculated by the one or more data processing units. The circuit board can additionally include a communications unit, configured, for example, to effect wireless communication between the data processing unit and a remote logging and or treatment observance system, such as a system implemented in the memory of a remote computing device, such as a mobile telephone or smartphone, or a remote or distributed server environment. The wireless communication unit can suitably be a Bluetooth unit, for example a Bluetooth low energy unit to minimize the battery power drain when providing such wireless communication, and a corresponding antenna. Alternatively, and/or additionally, the data processing system can be designed to communicate over a wifi link included in the data processing system, or any other suitable low power consumption communications system. The data processing system (18) further comprises an air sensor (57) located on a side of the circuit board (55) opposite to the data processing units and/or signal processing units and in air flow communication with an air sensor passage (58) integrated into the walls of the device body (4, 5). The air flow sensor passage (58) is separate to, and distinct from the drug flow passage (13), and extends through the device body (1) from the air flow sensor (57), generally underneath the drug flow passage (13), towards the exit orifice (14), where it exits the device body at a separate air sensor passage orifice (59). It is to be understood that the safety cap (17) when positioned on the MDI device (1) covers both the drug flow passage exit orifice (14) and the air flow sensor passage exit orifice (59), and that both exit orifices (14, 59) are configured and dimensioned such that a user's mouth can be appropriately positioned around said orifices (14, 59) without impairing inhalation by the user of any expelled drug. The air sensor (57) is connected to the circuit board and configured to operate therewith such that any change in air pressure due to inhalation, or in an opposite direction due to exhalation, by the user, from or into the device is duly detected and registered by the data processing unit. This advantageous feature of the device allows a user to be informed on the characteristics of any inhalation or exhalation effected through the MDI device in use, and the data obtained and processed by the data processing system is stored and/or communicated to the user via the wireless communication unit to a suitable display system, for example, such as is available on a smartphone via a corresponding software application or display program. Such a software application can provide, for example, data informing the user of how well the treatment regime assigned to the user is being followed, and/or assist the user in perfecting their inhalation technique so that the treatment regime is observed by the user under optimal conditions.

The power supply (60) is connected to the circuit board, and is, as already mentioned above, located in a suitable power supply housing (23). The power supply for such a device is minimal, and can adequately be provided by a battery, for example, a lithium battery, or alternatively a rechargeable battery. The power supply housing (23) and data processing system housing (22) are both closed by the device body wall (6), which is formed into a removable and click-fit or snap-fit cover, comprising, for example, projecting resilient hooks (61, 62) that extend from an inner surface of said wall (6) towards the power supply housing (23), and which engage with corresponding holes or slots (63, 64) provided in the power supply housing (23), and a battery cover (65), which engages with a corresponding area of the power supply housing, for example, via a projecting U-shaped edge (66) on the battery cover (65) slotting into a corresponding groove (67) located on the power supply housing (23). The data processing system (18) is inserted into the data processing system housing (22), the printed circuit board (55) being held between the cover of the device wall (6), and further comprises an electrical connector (68) configured to connect with a corresponding connector (69) provided by the correlation system (19), for example a magnetic electrical connector system, or alternatively spring-loaded electrical connectors, such as 854-series spring-loaded modular contact connectors available from Mill-Max Manufacturing Corp, USA.

Figure 5A:
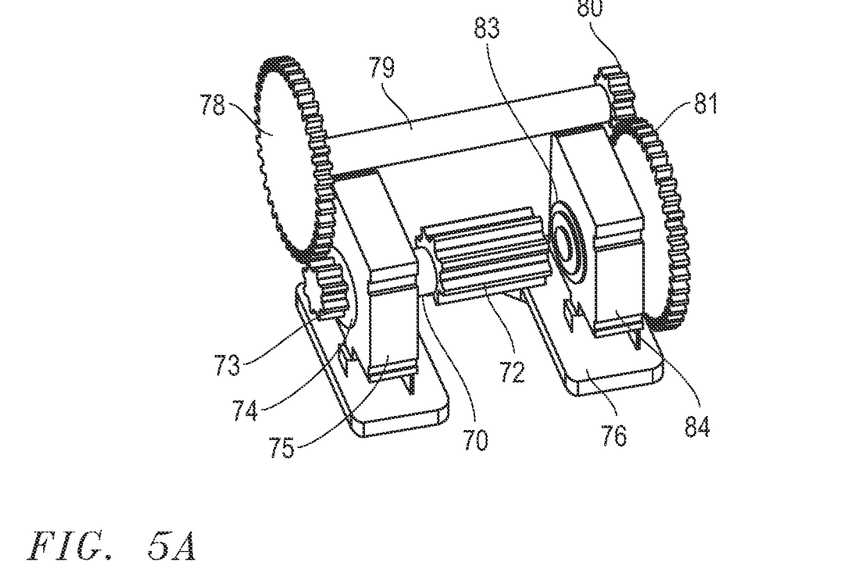
FIG. 5A is a schematic perspective view of a detail of the correlation system included in a metered dose inhaler (MDI) device according to the present invention.
Figure 5B:
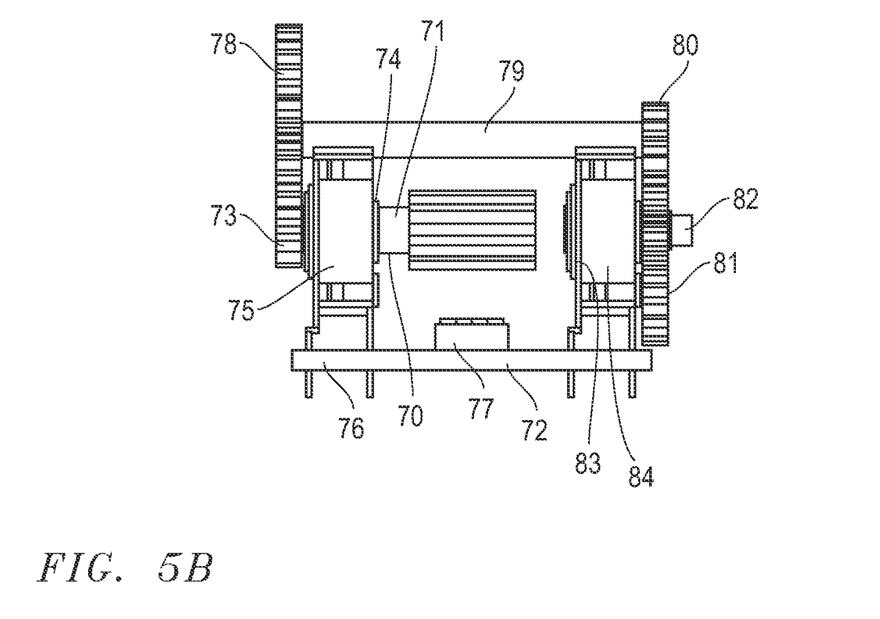
FIG. 5B is a schematic lateral view representation of the detail of FIG. 5A of the correlation system included in a metered dose inhaler (MDI) device according to the present invention.

FIGS. 5A and 5B show different schematic representations of the translation conversion means (31) provided by the correlation system (19), FIG. 5A being a perspective view of the translation conversion means (31) and FIG. 5B being a lateral, or side view of the same translation conversion means (31). The means (31) comprise a first axle shaft (70) having a peripheral surface (71) on which are defined a plurality or series of tooth-like projections (72). As can be seen in FIG. 1, the first axle shaft (70) is generally located beneath the stirrup (40), but is oriented orthogonally thereto as seen when viewed along the longitudinal axis of rotation of the first axle shaft (70). The first axle is mounted on, and maintained by first axle seating and locating projections (36, 37) provided on the lower housing component (33). These projections are suitably shaped to allow rotation of the first axle shaft (70) about its longitudinal axis of rotation. The first axle shaft (70) further comprises a toothed cog (73), located at an extremity of the first axle shaft (70) and distant from the plurality or series of tooth-like projections (72) located on the peripheral surface (71) of the first axle shaft (70). The first axle shaft also passes through an opening (74) in a first rotary potentiometer (75), which is configured to convert a rotational movement of the axle shaft (70) peripheral surface (71) into an electric potential, which can be either measured, and/or stored as a data value, when connected to an appropriate processing unit. The toothed cog (73) extends beyond the opening (74) provided in said at least first rotational position sensor (75), such that said toothed cog (73) is located outside of said at least first rotational position sensor. When the stirrup (40) is pushed down, via depression of the canister by the user, and corresponding bearing down of the shoulder (54) onto the shoulder (53) of the stirrup (40), the stirrup leg (43) and tip (42) move down towards the series or plurality of teeth (72) on the first axle shaft and engage with the surface of one of the teeth to push the engagement surface of the tooth downwards. As the first axle shaft (70) is maintained in a substantially horizontal position by the seating and locating projections (36, 37), it can not move down with the tip (42) of the stirrup, and so rotates around the axis of rotation. As the first axle shaft (70) rotates, the engagement surface of the teeth of the first axle moves out of engaging contact with the stirrup tip (42) and the tip (42) and stirrup (40) are free to be pushed back upwards under the recoil effect of the helical spring (52) to return to an unconstrained or relaxed position of the spring (52). The axle shaft peripheral surface (71) engages with the opening (74) of the first rotary potentiometer (75) which rotates correspondingly, and generates a readable or storable electrical potential, or value thereof. The first potentiometer is connected to a small printed circuit board (76), which comprises a data storage, such as a memory module, and/or data processing unit (77). The data processing unit and or data storage module (77) is powered via an electrical connector (69) also provided on the printed circuit board (76) and which connects to the printed circuit board of (55) of the data processing system (18). In this way, when the data processing system (18) is present in the MDI, data from the first potentiometer can be registered, stored, and/or processed and communicated via the electrical connector (69) to the data processing system.

The toothed cog (73) located at one extremity of the first axle shaft (70) engages with a toothed gear cog (78) located at a first extremity of a reducing gear cog system. The reducing gear cog also comprises a second axle shaft (79) and, located at an extremity of the second axle shaft opposite to the gear cog (78), a reducing gear toothed cog (80). The reducing gear toothed cog (80) engages with a toothed wheel visual display (81), which advantageously contains markings on an outer surface thereof (not shown), indicating the number of doses remaining and/or dispensed. As the first axle shaft rotates, so the first toothed cog (73) rotates, the first toothed cog (73) and first axle shaft being in fixed rotational relationship. Rotation of the first toothed cog (73) causes the toothed gear cog (78) to rotate, and consequently, the second axle shaft (79) in a corresponding manner. The second axle shaft (79), similar to the first axle shaft (70) is in a fixed rotational relationship with both gear cog (78) and reducing gear cog (80). Reducing gear cog (80) consequently rotates and engages with the toothed wheel (81) of the visual display causing it too, to rotate. A window is provided in the device body that is in register with a part of the visible surface showing a corresponding marking on the outer surface of the visual wheel display, so that the user can immediately see how many doses remain and/or have been used. This is useful as a rough guide for the user when the data processing system (18) is not plugged in and no power is being supplied to the electrical connector (69) of the printed circuit board (76). The reducing gear cog system (78, 79, 80) connected to the visual wheel display (81) thus provides a mechanical count of the number of expelled doses and/or doses remaining within the level of accuracy determined by the number of teeth in each cog and any corresponding mechanical play in the respective components. Additionally, the visual display wheel (81) is mounted on a third axle shaft (82) which is inserted into a central opening (83) of a second rotary potentiometer (84). The second rotary potentiometer is configured to generate an electric potential which corresponds to the rotational movement imparted by said visual display wheel which is in fixed rotational relationship with the third axle shaft (82). The second rotary potentiometer (84) is also connected to the second circuit board (76), and the data storage module and/or processing unit (77). First and second rotary potentiometers are advantageously configured to provide electric potentials or electrical signals corresponding to (a) angles of rotation limited to a single revolution of the potentiometer switch, and/or (b) angles of rotation representing multiple revolutions of the respective potentiometer switch. Preferably, the first rotary potentiometer is a single revolution rotary potentiometer, and the second potentiometer is a multi-revolution rotary potentiometer, the combined configuration of the two potentiometers enabling the data processing system (18) to distinguish between a sufficiently large number of distinct predetermined angles of rotation, each angle of rotation corresponding to a single dose dispensed by the canister. This allows for a variety of different drug canisters to be used in the MDI device, comprising a variety of total doses, with the assurance that each downward press of the canister will only be recorded once as an expelled dose by the data processing system or, if said data processing system is not connected for any reason, corresponding storage of the signals or values generated by the potentiometers will be effected to the storage module or data processing unit (77) provided on the second circuit board (76), pending the establishment of a renewed connection to the data processing system (18) and consequent recalculation of the effective dose expelled.

The invention claimed is:

1. Metered dose inhaler (MDI) device comprising a mechanically activated visual cue representing a number of doses expelled from, or doses remaining in, a drug-containing cartridge or canister locatable within a body of said MDI, said visual cue being visible through at least a portion of the body of said MDI, and a removable data processing system configured to verify the dose of drug administered and/or inhaled, wherein the MDI device further comprises a correlation system configured to correlate physically released doses from the drug containing cartridge or canister with the administration and/or inhalation data stored in the removable data processing system, wherein the correlation system comprises mechanical activation means in contact with a drug containing cartridge of the MDI device, and wherein said mechanical activation means engage with a translational movement conversion means configured to convert a translational movement of the mechanical activation means into a rotational movement;

wherein the correlation system further comprises at least a first rotational position sensor and at least a second rotational position sensor connected to the at least first rotational position sensor via a reducing gear, wherein the at least first rotational position sensor and the at least second rotational position sensor are configured to convert an angle of rotation into an electrical signal.

2. Metered dose inhaler (MDI) device according to claim 1, wherein the translational movement conversion means are connected to the at least first rotational position sensor.

3. Metered dose inhaler (MDI) device according to claim 1, wherein the at least first rotational position sensor is mechanically connected to the at least second rotational position sensor, and a rotational movement imparted to said at least first rotational position sensor is communicated to said at least second rotational position sensor.

4. Metered dose inhaler (MDI) device according to claim 1, wherein said at least second rotational position sensor is configured to have an angle of rotation indexed to the angle of rotation of the at least first rotational position sensor.

5. Metered dose inhaler (MDI) device according to claim 1, wherein said at least first rotational position sensor is configured to effect no more than one revolution of said sensor before a reset.

6. Metered dose inhaler (MDI) device according to claim 1, wherein said at least second rotational position sensor is configured to effect at least a plurality of revolutions of said sensor before a reset.

7. Metered dose inhaler (MDI) device according to claim 1, wherein said at least first rotational position sensor is connected to said at least second rotational position sensor via a visual display wheel mounted in coaxial rotational movement on said at least second rotational position sensor.

8. Metered dose inhaler (MDI) device according to claim 1, wherein said visual display wheel comprises a wheel outer surface, a portion of which is visible through the body of the MDI, and wherein said wheel outer surface comprises markings representative of a number of doses remaining, or expelled, from the drug containing cartridge.

9. Metered dose inhaler (MDI) device according to claim 1, wherein the correlation system further comprises a signal processing unit for processing signals received from the at least first rotational position sensor and/or the at least second rotational position sensor.

10. Metered dose inhaler (MDI) device according to claim 1, wherein the mechanical activation means in contact with a drug containing cartridge of the MDI device comprises a spring-loaded tongue having a first extremity and a second extremity, said first extremity engaging with a collar of said drug containing cartridge, and said second extremity engaging with the translational movement conversion means configured to convert a translational movement of the mechanical activation means into a rotational movement.

11. Metered dose inhaler (MDI) device according to claim 10, wherein the translational movement conversion means comprises an axle shaft having a peripheral surface, said peripheral surface being engaged by the second extremity of the spring loaded tongue at each activation of the drug-containing cartridge or canister, and imparting a rotational movement to said axle shaft.

12. Metered dose inhaler (MDI) device according to claim 11, wherein the peripheral surface of said axle shaft is provided with a plurality of peripheral teeth projecting from said peripheral surface, a different tooth of the plurality of peripheral teeth engaging with said second extremity of said tongue at each activation of the drug-containing cartridge or canister.

13. Metered dose inhaler (MDI) device according to claim 1, wherein the axle shaft further comprises a terminal toothed cog, located at an extremity of said shaft distant from said plurality of peripheral teeth.

14. Metered dose inhaler (MDI) device according to claim 1, wherein the axle shaft traverses and engages with an opening provided in said at least first rotational position sensor.

15. Metered dose inhaler (MDI) device according to claim 1, wherein the toothed cog extends beyond the opening provided in said at least first rotational position sensor.

16. Metered dose inhaler (MDI) device according to claim 1, wherein said removable data processing system comprises at least one air pressure sensor.

17. Metered dose inhaler (MDI) device according to claim 1, wherein said at least one air pressure sensor is located within the body of the MDI device in proximity to an air flow passage.

18. Metered dose inhaler (MDI) device according to claim 1, wherein said air flow passage is distinct from a passage for inhalation of expelled drug from the drug-containing cartridge.

19. Metered dose inhaler (MDI) device according to claim 1, wherein said removable data processing system is housed within a housing that is removable from and snap-fit insertable into, the body of the MDI device, and wherein said housing for said removable data processing system further comprises an electrical contact for establishing an electrical contact with the correlation system when said housing is inserted in the body of the MDI device.

* * * * *